United States Patent [19]

Scheele

[11] Patent Number: 5,162,209
[45] Date of Patent: Nov. 10, 1992

[54] SYNTHESIS OF FULL-LENGTH, DOUBLE-STRANDED DNA FROM A SINGLE-STRANDED LINEAR DNA TEMPLATE

[75] Inventor: George Scheele, Brookline, Mass.

[73] Assignee: Beth Israel Hospital Association, Boston, Mass.

[21] Appl. No.: 643,438

[22] Filed: Jan. 18, 1991

[51] Int. Cl.$^5$ .................. C12N 15/00; C12N 15/64; C12P 19/34
[52] U.S. Cl. .................. 435/91; 435/172.3; 435/320.1; 935/5; 935/7; 935/18; 935/80
[58] Field of Search .................. 435/91, 172.1, 172.3, 435/320.1; 536/27; 935/18, 7

[56] References Cited

U.S. PATENT DOCUMENTS

| | | | |
|---|---|---|---|
| 4,661,450 | 4/1987 | Kempe et al. | 435/91 |
| 4,985,359 | 1/1991 | Oberbaumer et al. | 435/91 |
| 4,987,073 | 1/1991 | Berman et al. | 435/91 |
| 5,023,243 | 6/1991 | Tullis et al. | 435/91 |

OTHER PUBLICATIONS

Ogilvie et al., J. Am. Chem. Soc. 99:7741–7743, 1977.
Usman et al., J. Am. Chem. Soc. 109:7845–7854, 1987.
Usman et al., Tetrahedron Letters 26:4567–4570, 1985.
Gubler et al., Gene 25:263–269, 1983.
Land et al., Nucleic Acids Research 9:2251–2266, 1981.
Okayama et al., Molecular and Cellular Biology 2:161–170, 1982.
Xu et al., DNA 6:505–513, 1987.
Strub et al., The EMBO Journal 3:2801–2807, 1984.
Schubert et al., Journal of Virology 51:505–514, 1984.
Stratagene (1990), pp. 58–59.
Gaubatz et al. (1982), J. Theor. Biol., vol. 95, pp. 679–696.

Primary Examiner—Richard A. Schwartz
Assistant Examiner—Richard M. Lebovitz
Attorney, Agent, or Firm—Fish & Richardson

[57] ABSTRACT

A method for preparing a ds DNA from a ss DNA template, which method includes:

(a) providing a first DNA strand;
(b) adding a homopolymeric oligonucleotide tail to the 3' end of the first DNA strand, to yield a tailed first DNA strand;
(c) providing a ss homopolymeric oligonucleotide primer complementary to a portion of the tail;
(d) contacting the primer with the tailed first DNA strand;
(e) synthesizing, in the presence of the primer and the tailed first DNA strand, a second DNA strand complementary to the first DNA strand; and
(f) removing the tail and the primer from the first and second DNA strands, respectively; provided that one or both of the tail and the primer contain(s) RNA.

8 Claims, 6 Drawing Sheets

SYNTHESIS OF FULL-LENGTH, DOUBLE-STRANDED DNA FROM A SINGLE-STRANDED LINEAR DNA TEMPLATE

BACKGROUND OF THE INVENTION

The field of the invention is synthesis of double-stranded DNA.

Conversion of a single-stranded ("ss") DNA template into a double-stranded ("ds") DNA molecule requires deoxynucleotide triphosphates ("dNTPs"), an enzyme capable of reading the template strand and incorporating the appropriate dNTPs into the complementary second DNA strand, and a primer able to provide a free 3' hydroxyl from which to start the second strand synthesis. This requirement for a primer has rendered difficult any attempt to synthesize a full-length second strand complementary to a linear template strand for which the nucleotide sequence at the 5' end is unknown, a problem that has been tackled in a variety of ways by researchers seeking to establish cDNA libraries (collections of cloning vectors into which have been cloned DNA copies of all or a selected fraction of the mRNA present in a sample of cells). Such libraries require the preparation of DNA species, termed "cDNA," complementary to all the mRNA species present in the cells. As described in detail by Maniatis et al. ("Molecular Cloning, A Laboratory Manual," Cold Spring Harbor Laboratory, Cold Spring Harbor, N.Y., 1982), preparation of ds cDNA from mRNA is a multistep process, beginning with the isolation of poly(rA)+mRNA from cells actively manufacturing proteins. [The term "poly(rA)" herein denotes an RNA homopolymer consisting entirely of adenosine ribonucleotide monophosphate (rAMP) units; "poly(dA)" would refer to a DNA homopolymer having adenosine deoxyribonucleotide monophosphate (dAMP) units. Each homopolymer made up of one of the other ribonucleotides or deoxyribonucleotides is herein represented in an analogous manner: e.g., "poly(rC)" is an RNA homopolymer made up of rCMP units; "poly(dC)" is a DNA homopolymer made up of dCMP units; "poly(rG)" is an RNA homopolymer made up of rGMP units; etc.]

The poly(rA)+mRNA species so isolated are then used as templates for the synthesis of cDNA, as follows: first, a synthetic poly(dT)-containing oligonucleotide is hybridized to the 3' poly(rA) tails of the mRNA molecules, where it serves as a primer for synthesis of the first strand of cDNA (sometimes termed the "antisense" strand) by a reverse transcriptase enzyme, using the mRNA as template. Under appropriate conditions, this enzyme can synthesize a full-length cDNA strand [i.e., a DNA strand complementary to the entire mRNA template, with the possible exception of some of the poly(rA) sequence at the 3' end of the mRNA], yielding a full-length ss cDNA hybridized to its mRNA template. These mRNA.cDNA hybrids may be directly cloned into vectors and used to transform host cells, but the low efficiency of this technique renders it "unsuitable for constructing large numbers of cDNA clones." (Maniatis et al., p. 221.) More frequently, cloning is accomplished using ds cDNA produced from the ss cDNA by any of several methods, including the following (illustrated in FIGS. 1-4, respectively):

(1) The mRNA cDNA hybrid is first treated with alkali to hydrolyze the mRNA, yielding ss cDNA. As ss cDNA will occasionally form, by self-hybridization of a few nucleotides at or near the 3' end of the molecule, transient "hairpin loops" (see FIG. 1) capable of priming synthesis of the second strand (the "sense" strand) of DNA from the 3' hydroxyl of the first strand, incubation of ss cDNA with DNA polymerase and all four dNTPs (i.e., dATP, dTTP, dCTP, and dGTP) for long periods (e.g., 20 hr) results in the conversion of many, if not all, of the ss cDNAs into ds cDNAs; the ss DNA loop joining the two complementary strands of the ds cDNA molecules may be removed with an endonuclease (such as $S_1$ nuclease) which specifically digests single-stranded DNA, yielding blunt-ended ds cDNA copies of the original mRNAs, minus varying amounts of each mRNA's 5' terminal sequence.

(2) Gubler and Hoffman (Gene 25:263-269, 1983) describe a procedure, illustrated in FIG. 2, in which a fragment of the original mRNA primes synthesis of the second DNA strand. The mRNA half of the mRNA.cDNA hybrid is randomly nicked by treatment with the enzyme RNase H, producing a number of 3' hydroxyl ends within the mRNA half of the hybrid, each of which can prime 5'- 3' DNA synthesis along the cDNA template. Nick translation by DNA polymerase generates a series of various-length DNA partial copies of the mRNA strand complementary to portions of the first cDNA strand. As the polymerase molecule synthesizing the DNA strand primed at the nick nearest to the 5' end of the original mRNA moves along the template, it degrades downstream mRNA fragments and nascent DNA strands, resulting in a ds hybrid having one full-length ss cDNA strand (the first cDNA strand) and a second strand that is partially varying lengths of mRNA (at the 5' end) and partially newly-synthesized DNA. In order to clone this molecule, the leftover mRNA portion is removed by residual RNase and the resulting ss DNA tail on the first strand is clipped off, leaving a blunt-ended ds cDNA missing some of the 5' terminal sequence of the original mRNA.

(3) Unlike the two methods described above, the method for ds cDNA synthesis reported by Land et al. (Nuc. Acids Res. 9:2251-2266, 1981) produces a ds cDNA copy of the entire mRNA, plus additional sequence that was not originally in that mRNA. The Land et al. method, illustrated in FIG. 3, begins with a ss cDNA from which the mRNA has been removed by alkaline hydrolysis. To the 3' end of this ss cDNA is added a poly(dC) tail, the synthesis of which is catalyzed by the enzyme terminal deoxyribonucleotidyl transferase (TdT). This homopolymeric tail at the 3' end of the first cDNA strand then serves as a site for hybridization with a complementary homopolymeric oligo-deoxynucleotide primer, oligo(dG). Second-strand DNA synthesis proceeds from the 3' hydroxyl of this primer, yielding a ds cDNA consisting of not only the full-length sequence of the original mRNA, but also a poly(dC.dG) extension at one end. Variations on this method which have been reported include combining a poly(dA) tail with an oligo(dT) primer, or a poly(dT) tail with an oligo(dA) primer. Regardless of which set of complementary deoxynucleotide homopolymers is used, the resulting homopolymeric extension, an artifact of the method used to generate the second cDNA strand, remains an integral part of the ds cDNA throughout the cloning procedure.

(4) A fourth method, reported by Okayama and Berg (Molec. Cellular Biol. 2:161-170, 1982) and illustrated in FIG. 4, also introduces a poly(dG.dC) tail onto one end of the ds cDNA. In this method, a ss poly(dT) tail is enzymatically added to the 3' end of one strand of a linearized ds DNA vector. Poly(rA)+mRNA is hybridized directly to this poly(dT) tail, positioning the 3' hydroxyl of the vector's poly(dT) tail to prime the synthesis of the first cDNA strand along the mRNA template. The 3' end of the newly-formed cDNA strand is then tailed with poly(dC), and a ds linker containing a ss poly(dG) tail is added to form a bridge between the two ends of the vector (see FIG. 4). Following treatment of this construct with DNA ligase and removal of the mRNA portion of the molecule, DNA polymerase is employed to generate the second cDNA strand, using the poly(dG) vector tail as primer and the first cDNA strand as template. Finally, DNA ligase closes the ds cDNA/vector circle, yielding a recombinant DNA vector containing full-length ds cDNA with a homopolymeric dG.dC extension at the 5' end of the "sense" strand. A variation on this method was described by Heidecker and Messing (Nucleic Acids Res. 11:4891–4904, 1983).

SUMMARY OF THE INVENTION

The method of the invention provides a novel way to make a ds DNA from a ss DNA template, which method includes (a) providing a first DNA strand;

(b) adding a homopolymeric oligonucleotide tail to the 3' end of the first DNA strand, to yield a tailed first DNA strand;

(c) providing a ss homopolymeric oligonucleotide primer complementary to a portion of the tail;

(d) contacting the primer with the tailed first DNA strand;

(e) synthesizing, in the presence of the primer and the tailed first DNA strand, a second DNA strand complementary to the first DNA strand; and (f) removing the tail and the primer from the first and second DNA strands, respectively; provided that one or both of the tail and the primer contain(s) RNA.

For example, where the tail includes DNA, the primer must include RNA (i.e., some or all of its nucleotide sequence is an RNA sequence), and where the primer includes DNA, the tail must include RNA; alternatively both the tail and the primer may include RNA. Table 1 sets forth the various combinations of specific homopolymers which may be used.

TABLE 1

| If the tail is: | the corresponding primer is: |
| --- | --- |
| poly(dC) | poly(rG) |
| poly(dG) | poly(rC) |
| poly(dA) | poly(rU) |
| poly(dT) | poly(rA) |
| poly(rC) | poly(rG) or poly(dG) |
| poly(rG) | poly(rC) or poly(dC) |
| poly(rA) | poly(rU) or poly(dT) |
| poly(rU) | poly(rA) or poly(dA) |

Each of the tail and the primer preferably is at least 5 nucleotides in length (more preferably 5 to 30 nucleotides, and most preferably 7 to 15 nucleotides).

Where the first DNA strand has a nucleotide sequence complementary to a portion of a strand of a naturally-occurring RNA (e.g., an RNA virus or an mRNA), the invention provides a method of making a full-length, ds cDNA from that first DNA strand. The method of the invention can be used to generate a cDNA library useful for cloning experiments if the first DNA strand is complementary to an mRNA or a fragment of an mRNA; in this case the method would include the additional step of inserting the full-length ds cDNA product into a cloning vector.

Also within the invention is a primer which consists of a substantially purified, ss homopolymeric oligoribonucleotide [e.g., poly(rG), poly(rC), poly(rU) or poly(rA)] at least 5 (preferably between 5 and 30) ribonucleotides in length. This primer may be part of a kit useful for converting a ss linear DNA strand into a ds DNA duplex (or a ss RNA strand such as mRNA into first a ss linear DNA strand and then into a ds DNA duplex), which kit might also include a first enzyme (e.g., TdT or polyA polymerase) capable of adding a homopolymeric tail to the 3' end of the ss linear DNA strand; a second enzyme (e.g., E.coli DNA Polymerase I) capable of synthesizing DNA complementary to a DNA template; and, optionally, instructions for using the kit. The kit could additionally include a preparation containing a single deoxynucleotide triphosphate (e.g., a dNTP selected from dCTP, dGTP, dATP and dTTP), which can be polymerized by the first enzyme into a homopolymeric ss DNA tail complementary to the primer provided with the kit; a mixture of four dNTPs for use with the second enzyme; a third enzyme (e.g., RNase H) capable of removing RNA from an RNA.DNA duplex without significant degradation of the DNA portion of the duplex; and, optionally, a fourth enzyme (e.g., T4 polymerase) capable of digesting a ss DNA tail attached to one strand of a ds DNA molecule.

The method of the invention offers several advantages over traditional methods of synthesizing ds DNA from a ss DNA strand. By utilizing a 3' tail or primer which is RNA, known methods of hydrolyzing RNA (e.g., enzymatically or by the use of high pH) can be employed, after synthesis of the second DNA strand, to remove selectively the RNA portion of the homopolymeric extension from the ds DNA duplex. This leaves either no extension (if both the tail and the primer were RNA), or a ss DNA extension (if either the tail or the primer was DNA) which can be readily removed with an appropriate ss-specific DNA nuclease. The net result is a blunt-ended ds DNA without an extraneous homopolymeric DNA.DNA extension to contribute experimental artifacts such as interference with cloning and expression of cDNA (Xu et al., DNA 6:505–513, 1987). In addition, unlike other frequently-used methods, the method of the invention does not result in the loss of any sequence corresponding to the 3' end of the original ss DNA strand (or the 5' end of the original RNA template, if the ss DNA strand was generated by reverse transcription of an RNA such as mRNA). When used to produce ds cDNA copies of mRNA, the full-length ds cDNA that is generated by the method of the invention preserves all of the 5' untranslated region present on the original mRNA and potentially necessary for full expression efficiency of the cloned cDNA. The resulting full-length ds cDNA can be cloned and expressed with higher efficiency than ds cDNA obtained by previously-known methods.

Furthermore, the kit of the invention offers a convenient way to practice the method of the invention, in order to obtain a full-length ds DNA from any given ss DNA strand.

Other features and advantages of the invention will be apparent from the following description of the preferred embodiments, and from the claims.

DETAILED DESCRIPTION

The drawings are first described.

DRAWINGS

Figure 6:

FIG. 6 is an autoradiogram of an alkaline electrophoretic gel in which lane 1 represents DNA size markers, lanes 2 and 6 represent full-length first (antisense) cDNA strands reverse-transcribed from a dog pancreatic mRNA preparation, and lanes 3, 4, and 5 represent second (sense) cDNA strands made from the same mRNA preparation according to the method of Lane et al. (lane 3), the method of Gubler and Hoffman (lane 5), or the method of the invention (lane 4).

PREPARATION OF FULL-LENGTH DS DNA FROM A SS DNA TEMPLATE

Figure 5:
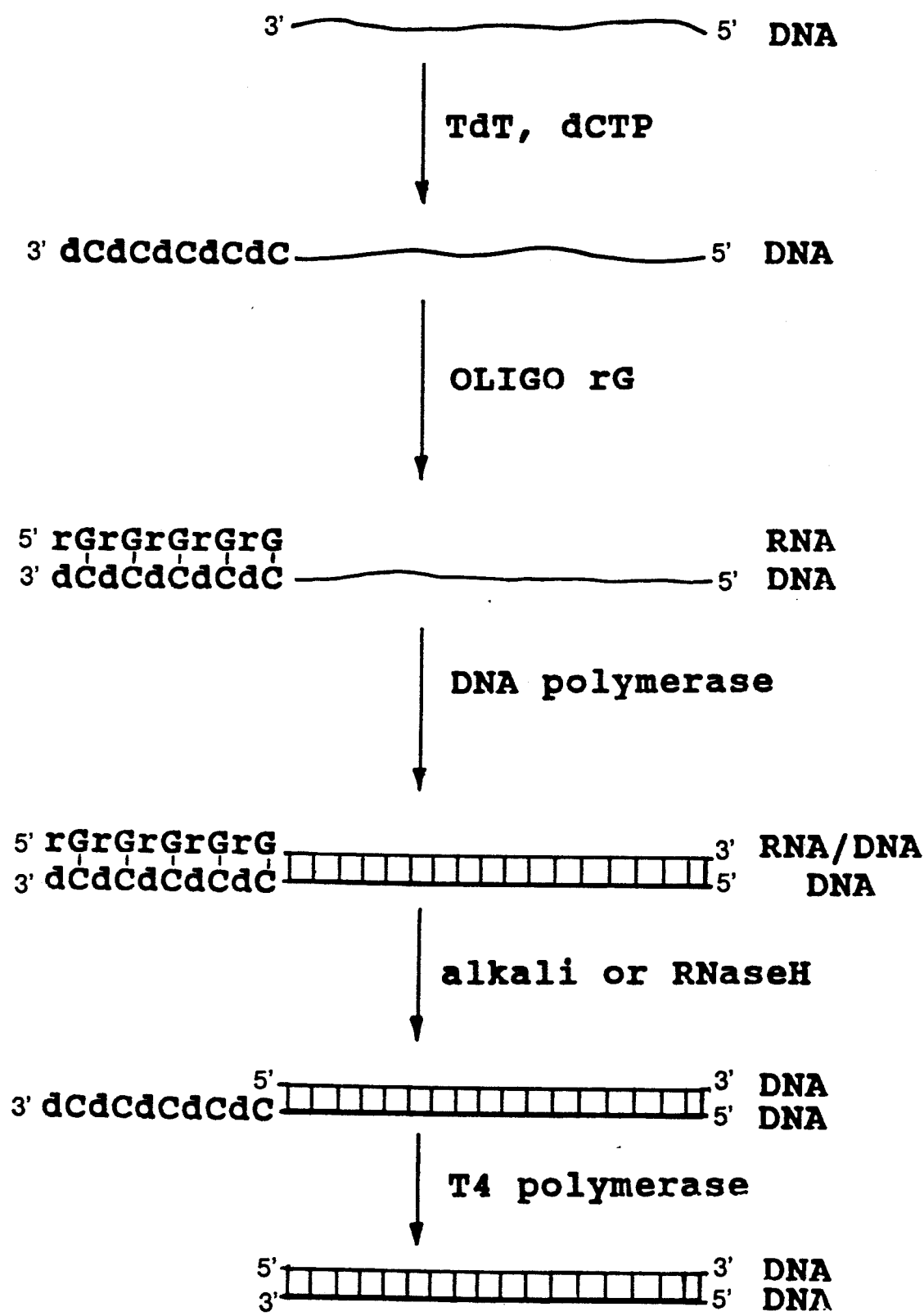
FIG. 5 is an illustration of one embodiment of the method of the invention.

The method illustrated in FIG. 5 involves the following steps:

(a) Starting with a first ss DNA strand [which may be, for example, denatured genomic DNA, a ss DNA virus, or DNA synthesized from an RNA template (such as mRNA or an RNA virus)], a homopolymeric oligonucleotide tail is added to the 3' end of the DNA strand. This tail is generally attached to the 3' end of the ss DNA strand via sequential addition of nucleotides by an enzyme such as TdT or polyA polymerase, although ligation of a suitable pre-formed homopolymeric oligonucleotide to the 3' end of the DNA strand would also suffice. The tail may be DNA [poly(dC), poly(dG), poly(dA), or poly(dT)] or RNA [poly(rC), poly(rG), poly(rA), or poly(rU)]. In the Example described below, the tail is poly(dC). A poly(dC) tail has been shown to offer some advantages over a tail comprising poly(dG), which in ss form can condense into a nonproductive secondary structure that produces experimental artifacts (such as difficulty in hybridizing to a complementary primer); additionally, the rate of tail synthesis by TdT (and thus tail length) is more readily controlled by time and temperature manipulations when dCTP is the nucleotide used than when dGTP is the nucleotide. A poly(dC) tail is also somewhat superior to poly(dA), poly(dT), poly(rA) and poly(rU) tails because the three hydrogen bonds formed in each G·C pair provide more hybridization stability than do the two hydrogen bonds formed between A·T or A·U pairs. Furthermore, a poly(dC) tail means that the primer would be poly(rG), which is more resistant to contaminating RNAse A than would be a primer of poly(rC) or poly(rU). The precise length of the tail is not critical, provided that it is long enough to hybridize efficiently and stably with the primer (i.e., at least five nucleotides long). A range of approximately 5 to 30 nucleotides is recommended for the length of the tail.

(b) A single-stranded homopolymeric oligonucleotide primer complementary to the tail is then allowed to hybridize with the tail. In order to provide a means for readily removing the primer and tail after synthesis of the second DNA strand, either the primer or the tail (or both) must be RNA. Thus, if the tail is RNA, the primer may be either RNA or DNA; if the tail is DNA, the primer must be RNA. The identity of the homopolymer comprising the primer is of course dependent upon the identity of the homopolymer comprising the tail, with all of the possible tail/primer combinations shown in Table 1 above. The primer may be of synthetic or natural origin. The length of the primer is not critical, provided that it is long enough to hybridize efficiently and stably with the tail (i.e., at least five nucleotides long). A range of 5 to 30 nucleotides is recommended for the primer. The primer utilized in the Example below was oligo(rG)$_{15}$ (i.e., an RNA oligomer consisting of 15 guanosine ribonucleotide monophosphate units).

The primer may be shorter than, longer than, or the same length as the tail, although where the tail is DNA, a primer at least as long as the tail is preferred in order to minimize the possibility that, even after the primer is fully hybridized to the tail, one or more nucleotides at the 5' end of the tail remain unhybridized (whether due to a short primer or to an uneven match of the primer and the tail). If this should occur, subsequent synthesis of the second DNA strand will start with the incorporation of deoxynucleotides complementary to the unhybridized portion of the tail. This would result (if the tail is DNA) in a ds DNA molecule having at one end a ds homopolymeric extension of one or more DNA base pairs. A very short extension (i.e., fewer than five base pairs) will generally have an insignificant impact on the outcome of the cloning experiment. However, one could avoid this problem entirely by either (1) ensuring that the tail is a homopolymer of RNA rather than DNA, or (2) if the tail is a homopolymer of DNA, including the following step after hybridization of the primer to the tail of the first strand, and prior to addition of DNA polymerase and dNTPs: add an RNA polymerase and one rNTP, the same rNTP that comprises the primer. This permits the extension of the RNA primer right up to the 5' end of the tail, where RNA synthesis will cease in the absence of the other three rNTPs. At this point DNA polymerase can be added with the four dNTPs so that DNA synthesis can pick up where RNA synthesis left off. Subsequent removal of the RNA primer will also remove the portion synthesized in situ by RNA polymerase, leaving the entire DNA homopolymer tail susceptible to digestion by an appropriate nuclease specific for ss DNA.

RNA is notoriously sensitive to degradation by ubiquitous RNases. Therefore, great care must be taken in handling oligo(rG) or any other RNA homopolymer primer, in order to prevent contamination with RNase and loss of the primer. Even where the usual precautions are taken, a stored preparation of RNA primer can be expected to be gradually degraded, and thus to lose (over a period of months) its effectiveness as a primer for DNA synthesis.

(c) Once an appropriate primer is hybridized to the first DNA strand (and, if necessary, RNA polymerase has transcribed the unhybridized 5' end of the tail), the second full-length DNA strand is synthesized by adding DNA polymerase and all four dNTPs to the primed template.

(d) The portion of the resulting double stranded nucleic acid which is RNA (either the primer or the tail or both) can then be removed [e.g., using RNAse H where only one of the primer or tail is RNA, or a ds RNase (such as cobra venom ds RNase) where both the primer and tail are RNA]. If either the primer or the tail is DNA, it will thereupon be rendered single-stranded, and can conveniently be removed using an appropriate ss DNA nuclease: e.g., T4 polymerase will remove a 3' ss DNA overhang, as where the tail is DNA, while other nucleases (such as S1 nuclease, mung bean nuclease, and Exonuclease VII) are useful for removing a 5' ss DNA overhang, as where the primer is DNA. This removal of any ss DNA overhang left after removal of the RNA primer or tail results in a blunt-ended, full-length ds DNA suitable for further experimentation, including cloning.

EXAMPLE

Poly(rA)+mRNA was isolated from dog pancreatic cells and purified on a poly(dT) column by standard methods. Incubation with avian myeloma virus (AMV) reverse transcriptase (Stratagene, La Jolla, Calif.) and an oligo(dT) adaptor-primer (Stratagene) in the presence of all four dNTPs, in accordance with standard methods, converted the mRNAs into cDNA·RNA hybrids. Alkaline hydrolysis of the mRNA (50 mM NaOH) yielded ss cDNA, the 3' end of which was then tailed with poly(dC) as follows: 2 μg ss cDNA in 2 μl H$_2$O was added to 4 μl 5×TdT buffer (0.5M potassium cacodylate, pH 7 2, 10 mM CoCl$_2$, 1 mM DTT), 2 μg BSA in 2 μl H$_2$O, 4 μl 250 μM dCTP, 15U TdT enzyme (BRL, Bethesda, Md.) in 1 μl H$_2$O, and 7 μl H$_2$O. After 1.5 min at 22° C., the tailing reaction was stopped by adding 1 μl 0.5 M EDTA. The tailed ss cDNA was ethanol-precipitated and resuspended in TE (10 mM TrisHCl, pH 7.5, 1 mM EDTA) at 100 ng DNA/μl. Under these conditions, approximately 15 nucleotides are sequentially added to the 3' end of ss DNA by TdT.

The poly(dC)-tailed ss cDNA was primed for second-strand DNA synthesis by combining 1-2 μg of the poly(dC)-tailed ss cDNA (in 2 μl TE), 100 ng oligo(rG)$_{15}$ primer (Peninsula Laboratory, Inc., Belmont, Calif.) in 1 μl TE, 5 μl 1 M HEPES, pH7.5, 1.25 μl 2M KCl, and 3 μl 0.1 M MgCl$_2$, at 65° C. for 2 min; the reaction mixture was then slowly cooled down (~1 hr) to 16° C.

Second-strand cDNA synthesis was carried out as follows: to the hybridization reaction mixture described above was added 0.5 μl 1M DTT; 1.25 μl each 10 mM dATP, 10 mM dTTP, 10 mM dGTP, and 10 mM dCTP; 2.5 μl DNA Polymerase I (3.85 U/μl; Stratagene) and 1.75 μl H$_2$O. [If subsequent analysis of the second-strand chain length is desired, the nucleotide mixture can include a label such as α$^{32}$P-dCTP (30 μCi; 800 Ci/mmole) diluted in 0.5 μl 10 mM dCTP, instead of the full 1.25 μl of 10 mM dCTP.] The reaction proceeded at 16° C. for 3 hr, after which the Pol I enzyme was inactivated (and subsequent snap-back prevented) by heating to 70° C. for 15 min. These and the other temperature manipulations described below can be conveniently carried out by the use of a machine designed to control temperature for polymerase chain reaction (PCR) experiments (Perkin-Elmer/Cetus).

Figure 1:
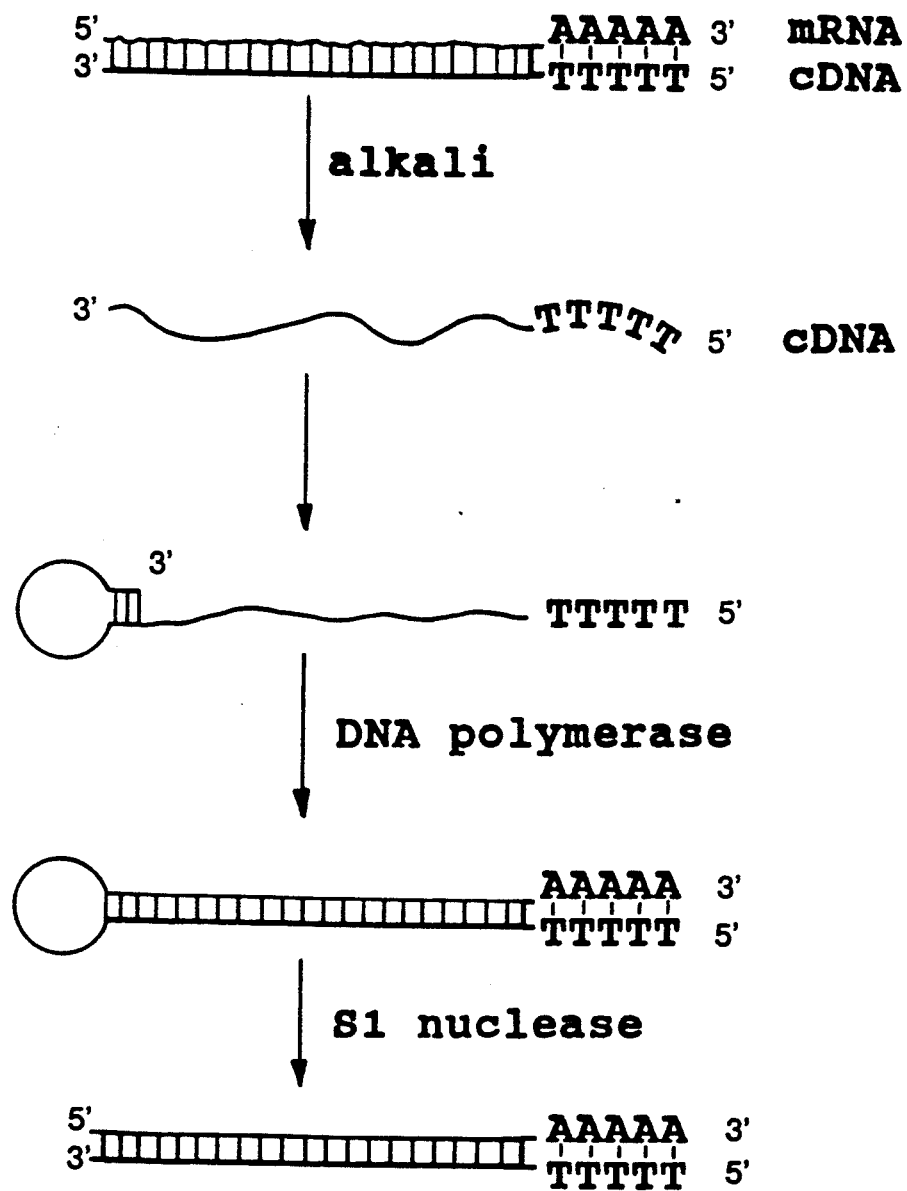
FIG. 1 is an illustration of a traditional method of preparing ds cDNA.
Figure 2:
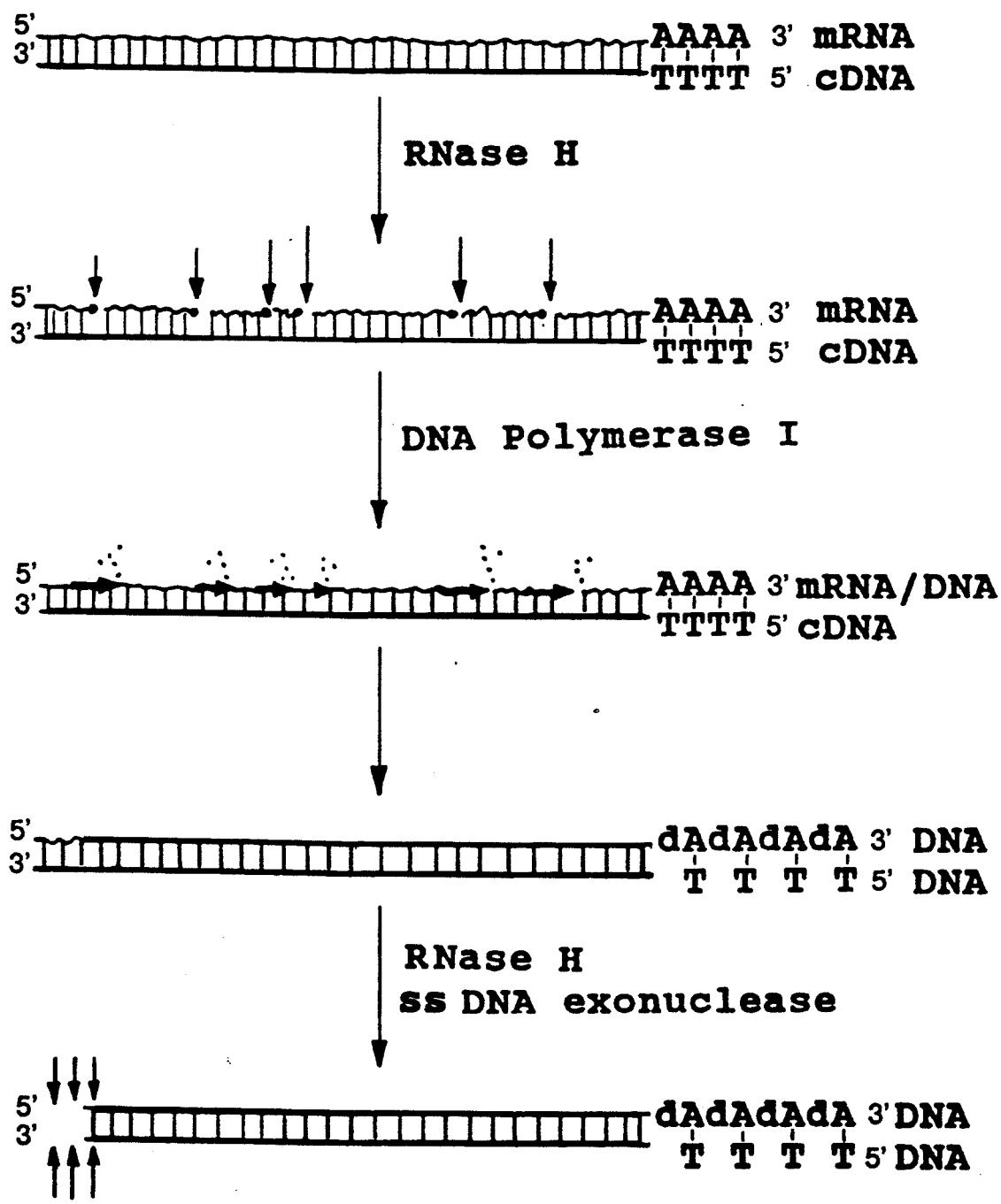
FIG. 2 is an illustration of a second traditional method of preparing ds cDNA.
Figure 3:
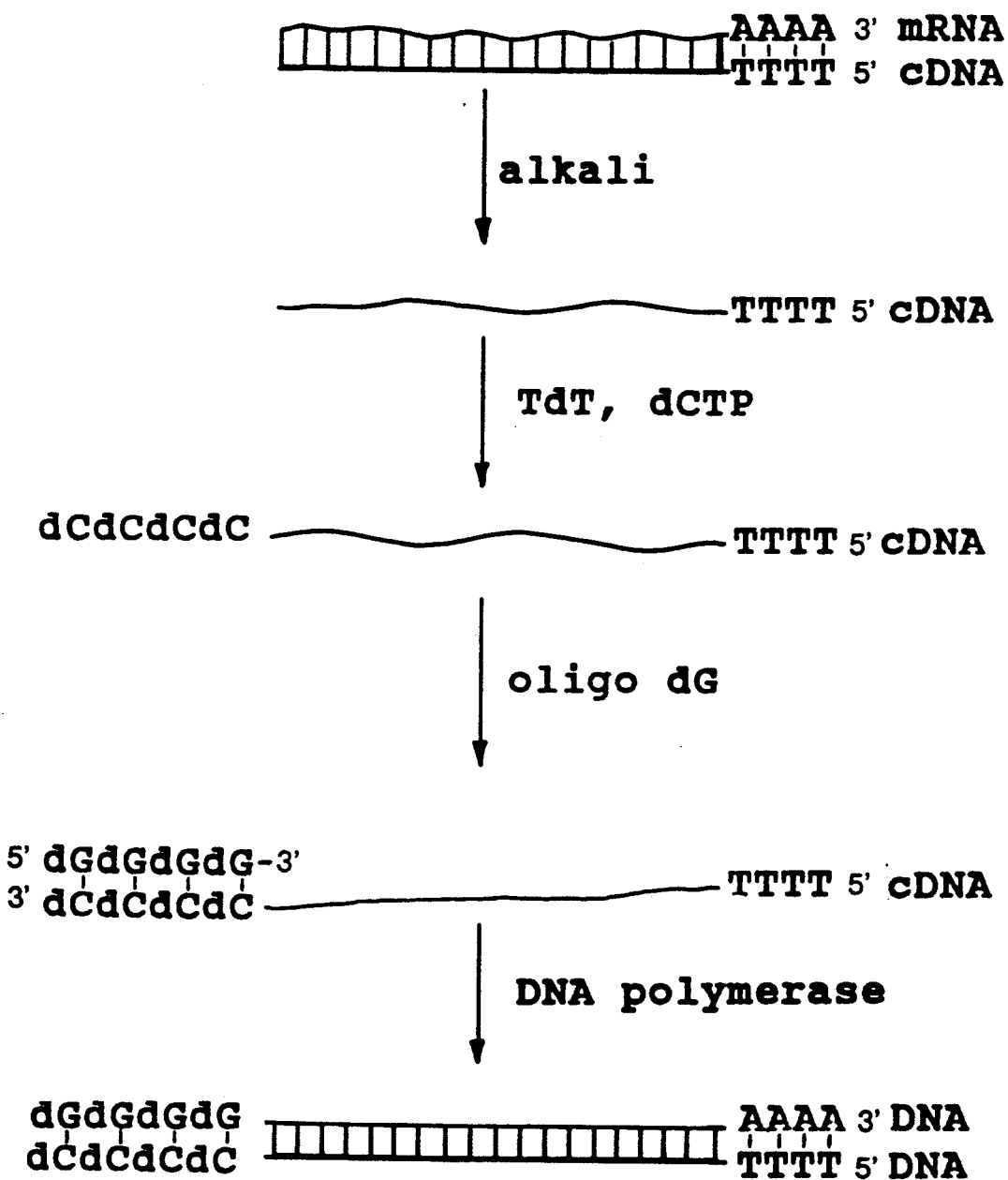
FIG. 3 is an illustration of a third traditional method of preparing ds cDNA.
Figure 4:
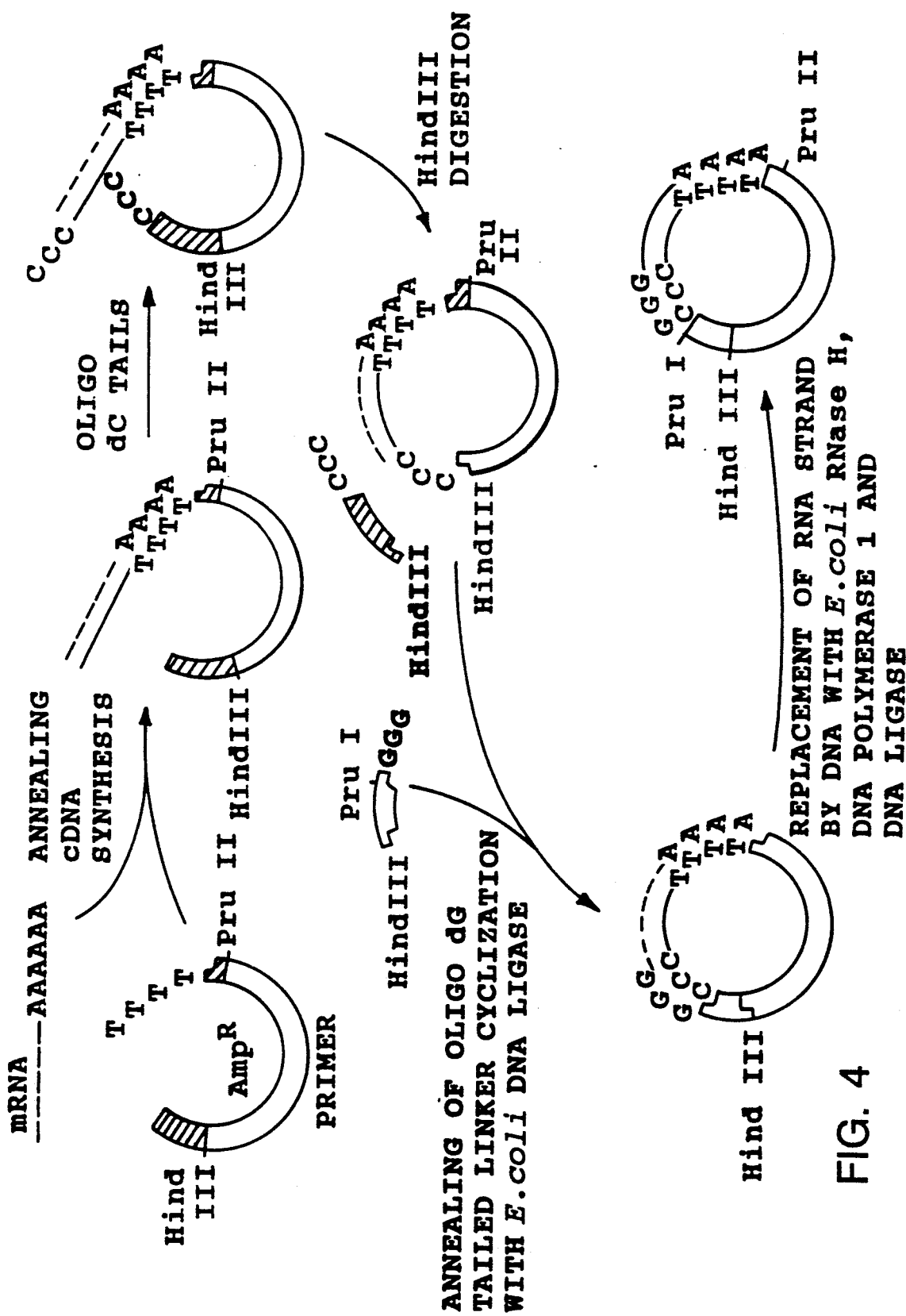
FIG. 4 is an illustration of a fourth traditional method of preparing ds cDNA (adapted from FIG. 2 of Okayama and Berg, p. 163).

The next step is to remove the homopolymeric primer and tail. The oligo(rG)$_{15}$ primer, which at this point comprises the 5' end of the second DNA strand, is removed from the duplex molecule by treatment with the enzyme RNase H; simultaneously the poly(dC) tail is removed by the 3'-5' exonucleolytic activity of T4 polymerase. The reaction conditions are as follows: 20 μl of the heat-killed DNA Polymerase I reaction mixture containing ds cDNA with the poly(dC).poly(rG) extension was combined with 2.5 U RNase H (2.5 U/μl; BRL) and 2.4 U T4 polymerase (2.4 U/μl; Stratagene), and incubated at 37° C. for 30 min, following which the T4 enzyme was inactivated by heating the reaction mixture to 70° C. for 15 min. The reaction product (ds blunt-ended cDNA) was then purified by phenol-extraction and ethanol-precipitation. In order to judge the effectiveness of this method for producing full-length ds cDNA, parallel procedures were separately carried out with radiolabelled α$^{32}$P-dCTP as part of the reaction mixture for synthesizing either the first (antisense) or the second (sense) strand of cDNA from the dog pancreatic mRNA preparation. After the ds cDNA was prepared and homopolymeric extensions removed in each case, the resulting ds cDNAs were denatured and compared by electrophoresis on parallel lanes of an alkaline gel. As shown in FIG. 6, radiolabelled second strands made by the method of the invention (lane 4) have the same size distribution as radiolabelled first strands reverse transcribed from the same mRNA preparation (lanes 2 and 6). Furthermore, second cDNA strands prepared by the method of Land et al. (lane 3) and the method of Gubler and Hoffman (lane 5) were compared to that prepared by the method of the invention (lane 4). Land et al.'s method (described above and illustrated in FIG. 3) results in a second cDNA strand with a 5' homopolymeric DNA extension, consistent with the increased length of the DNA strands observed in lane 3 compared to those in lanes 2, 4, and 6. In contrast, Gubler and Hoffman's technique (described above and illustrated in FIG. 2) results in a second cDNA strand (lane 5) shorter than the second strands made by the method of the invention (lane 4).

RNase H/T4 polymerase-treated ds cDNA, prepared according to the method of the invention in a separate experiment in which the dCTP incorporated into the poly(dC) tail was radiolabelled, was also analyzed by alkaline gel electrophoresis. This experiment indicated that almost all (~98%) of the radiolabelled DNA tail is removed by the RNase H/T4 procedure described above (data not shown).

USE

The method of the invention is useful for converting any ss DNA strand into a full-length ds DNA, even if the sequence at the 3' end of the ss DNA strand is unknown. This method has wide applicability in the field of cDNA cloning, as it permits cloning of a ds cDNA representing the entire mRNA sequence, including the entire 5' untranslate region, without introducing into the clone long stretches of homopolymeric DNA that may interfere with cloning and expression of the cDNA. It is also useful for making full-length ds DNA from other sources of ss DNA, such as ss DNA viruses, any denatured DNA, or reverse transcripts of RNA viruses and other RNAs.

The method could be adapted to permit amplification of a sample of ds DNA (such as ds cDNA) by PCR, as follows: to a sample of ds cDNA prepared by the method of the invention, with its RNA primer/DNA tail extension still intact, is added excess RNA primer (identical to the RNA primer used to generate the original ds cDNA) and excess oligo(dT) primer, in a reaction mixture with an appropriate temperature-stable DNA polymerase (e.g., Taq) and all four dNTPs; the mixture is subjected to an appropriate number of PCR temperature cycles in a PCR machine (e.g., 40 cycles) in accordance with standard PCR procedures. Following this amplification of the ds cDNA, the RNA.DNA homopolymeric extensions on each ds cDNA molecule so generated can be removed with RNase H and T4 polymerase, as described in the Example given above. Alternatively, one could start with just a ss DNA strand, add a 3' homopolymeric DNA tail to the ss DNA strand using TdT, and produce multiple ds DNA copies from this tailed ss DNA by the PCR procedure outlined above.

OTHER EMBODIMENTS

Other embodiments are within the following claims. For example, the elements essential for practicing the invention could be combined in kit form, which kit would be within the invention. Such a kit might include (a) an enzyme (such as TdT) and an rNTP or dNTP (such as dCTP) for adding a homopolymeric tail to the 3' end of the ss DNA;

(b) an appropriate homopolymeric RNA (or DNA, if the tail is RNA) primer [such as oligo(rG)$_{15}$];

(c) a DNA polymerase (such as DNA Polymerase I) and dNTP mixture for synthesizing the second strand;

(d) a means for removing (1) an RNA.RNA homopolymeric extension, such as by the use of NaOH or a ds RNase, or (2) an RNA.DNA homopolymeric extension, such as by the use of (i) the enzymes RNase H and T4 polymerase or (ii) NaOH and a ss DNA exonuclease or endonuclease; and (e) instructions for using the kit.

What is claimed is:

1. A method of making a ds DNA, said method comprising the following steps:

(a) providing a first ss DNA strand;
    (b) adding to the 3' end of said first DNA strand a homopolmeric oligonucleotide tail comprising five deoxyribonucleotides, to yield a tailed first DNA strand;
    (c) providing a ss homopolymeric RNA primer complementary to a portion of said tail, said primer comprising five ribonucleotides;
    (d) contacting said primer with said tailed first DNA strand;
    (e) synthesizing, in the presence of said primer and said tailed first DNA strand, a second DNA strand complementary to said first DNA strand and having said primer at its 5' end;
    (f) after said synthesizing step, hydrolyzing said primer enzymatically or by the use of high pH, leaving said tail single-stranded; and
    (g) enzymatically removing said ss tail from said first DNA strand, to yield a full-length ds cDNA.

2. A method of making a full-length, ds cDNA, said method comprising the method of claim 1; provided that said first DNA strand comprises a nucleotide sequence complementary to a strand of a naturally-occurring RNA.

3. A method of making a cDNA library, said method comprising the method of claim 2 and further comprising the step of inserting said full-length ds cDNA into a cloning vector, provided that said naturally-occurring RNA is an mRNA.

4. The method of claim 1, wherein
    (a) said tail comprises poly(dC), and
    (b) said primer comprises poly(rG).

5. The method of claim 1, wherein
    (a) said tail comprises poly(dG), and
    (b) said primer comprises poly(rC).

6. The method of claim 1, wherein
    (a) said tail comprises poly(dA), and
    (b) said primer comprises poly(rU).

7. The method of claim 1, wherein
    (a) said tail comprises poly(dT), and
    (b) said primer comprises poly(rA).

8. The method of claim 1, wherein said primer comprises between 5 and 30 nucleotides.

* * * * *

UNITED STATES PATENT AND TRADEMARK OFFICE
CERTIFICATE OF CORRECTION

PATENT NO. : 5,162,209

DATED : November 10, 1992

INVENTOR(S) : George Scheel and Shin-Ichi Fukuoka

It is certified that error appears in the above-identified patent and that said Letters Patent is hereby corrected as shown below:

On the title page item [75] add the following inventor:
Shin-Ichi Fukuoka, Boston, Mass.

Signed and Sealed this

Fifth Day of October, 1993

*Attest:*

BRUCE LEHMAN

*Attesting Officer*  Commissioner of Patents and Trademarks